United States Patent
Sturm

(10) Patent No.: US 6,180,393 B1
(45) Date of Patent: Jan. 30, 2001

(54) WATER-SOLUBLE CONTACT LENS CARE PRODUCT

(76) Inventor: Albert Sturm, Lortzingstrasse 33, D-50931 Köln (DE)

( * ) Notice: Under 35 U.S.C. 154(b), the term of this patent shall be extended for 0 days.

(21) Appl. No.: 09/380,319

(22) PCT Filed: Feb. 27, 1998

(86) PCT No.: PCT/EP98/01109

§ 371 Date: Oct. 26, 1999

§ 102(e) Date: Oct. 26, 1999

(87) PCT Pub. No.: WO98/37921

PCT Pub. Date: Sep. 3, 1998

(30) Foreign Application Priority Data

Feb. 28, 1997 (DE) .............................................. 197 08 135
Jul. 11, 1997 (DE) .............................................. 197 29 831

(51) Int. Cl.[7] .............................. C12S 9/00; A61L 2/23; C11D 3/48
(52) U.S. Cl. .............................. 435/264; 134/42; 134/901; 206/5.1; 422/28; 422/30; 510/114
(58) Field of Search .................. 206/5.1, 524.7; 422/28, 30, 300, 301; 134/27, 28, 42, 901; 435/188, 264; 510/113, 114, 115, 112

(56) References Cited

U.S. PATENT DOCUMENTS

| | | | |
|---|---|---|---|
| 4,568,517 | * | 2/1986 | Kaspar et al. ............................ 422/30 |
| 4,748,992 | * | 6/1988 | Giefer ............................... 422/301 X |
| 4,863,627 | * | 9/1989 | Davies et al. ......................... 422/28 X |
| 5,011,661 | * | 4/1991 | Schafer et al. .......................... 422/30 |
| 5,312,588 | * | 5/1994 | Gyulai et al. ........................... 422/30 |
| 5,384,091 | * | 1/1995 | Rontome et al. ........................ 422/30 |
| 5,556,480 | * | 9/1996 | Rontome et al. .................... 134/42 X |
| 5,723,096 | * | 3/1998 | Bruun-Jensen ........................ 422/301 |
| 5,759,540 | * | 6/1998 | Nielsen .............................. 134/901 X |
| 5,766,931 | * | 6/1998 | Cook et al. .......................... 422/30 X |
| 5,897,833 | * | 4/1999 | Hunt et al. .............................. 422/28 |
| 5,919,698 | * | 7/1999 | Sorensen et al. ................... 422/28 X |
| 6,022,732 | * | 2/2000 | Bakhit et al. ....................... 422/30 X |

FOREIGN PATENT DOCUMENTS

| | | |
|---|---|---|
| 0 209 071 | 1/1987 | (EP) . |
| 0 219 220 | 4/1987 | (EP) . |
| WO 91 12826 | 9/1991 | (WO) . |
| WO 97 11722 | 4/1997 | (WO) . |

* cited by examiner

Primary Examiner—Bryon P. Gehman
(74) Attorney, Agent, or Firm—Collard & Roe, PC

(57) ABSTRACT

A water-soluble, solid contact lens care agent (1) having at least a first (2) and a second (3) compartment containing within the first compartment (2) at least one agent, in particular a protease, for removing or supporting the cleaning of metabolic deposits on a contact lens and within the second compartment (3) at least one agent being capable of neutralizing a contact lens disinfecting solution, characterized in that the first compartment (2) is dissolved faster within the contact lens disinfecting solution than the second compartment (3) and both compartments (2, 3) are simultaneously subjectable to the contact lens disinfecting solution.

9 Claims, 1 Drawing Sheet

WATER-SOLUBLE CONTACT LENS CARE PRODUCT

BACKGROUND OF THE INVENTION

1. Field of the Invention

Subject matter of the present invention is a water-soluble, solid contact lens care agent.

2. The Prior Art

Contact lenses are much in demand with individuals suffering from ametropia. Still, one problem with the use of contact lenses is the correct care thereof. There is known a multitude of different systems having essentially in common that a disinfection of the contact lens is effected after wearing the contact lens, usually during the night, where disinfection is effected by chemicals which have to be neutralized subsequently due to the aggressive character thereof. For this purpose a multiplicity of care agents has been successful on the market, e.g., an aqueous hydrogen peroxide solution as disinfecting solution which is neutralized or decomposed by subsequent steps. To this end, several systems such as the catalytic decomposition on precious metal surfaces, the enzymatic decomposition using, e.g., catalase, and the chemical neutralization by reduction of the hydrogen peroxide by sodium thiosulfate are known in the art. The problem of removing metabolic deposits, in particular protein deposits on the lenses or within the lens material, has in principle been solved in the art as well. For this, e.g., agents containing protease are added during a preliminary cleaning step. In particular, subtilisin has to be mentioned as a protease removing any protein deposits within the matrices of soft contact lenses. The state of the art is represented by EP 0 219 220. There, a combined contact lens care agent is described which both disinfects and cleans the contact lenses. In this case, a solution of hydrogen peroxide and a protease being active in a peroxide-containing solution effects disinfection. As a suitable protease subtilisin is mentioned.

Removing any metabolic deposits, in particular protein deposits, within the contact lens matrices is extremely important as these deposits result in changes of the lens matrix including changes of the optical properties and the generation of inflammations.

Although various systems have been available in the market, caring especially for soft contact lenses seems to be so complicated that recently so-called one-way contact lenses have been marketed increasingly. Here, cleaning and disinfecting is no longer in the fore as the contact lenses are simply disposed after a certain wearing time. On the other hand, this results in the fact that only ready-made, mass-produced articles can be offered as any individual adaption of the contact lens is too costly, so that an individually adapted one-way lens will be unattainable. However, when dispensing with individual adaptions patients are provided with contact lenses lacking optimal properties, so that such a way of proceeding is not advisable from the physiological point of view.

The state of the art is especially detrimental in that proteases are usually employed in a separate cleaning step which is arranged prior to the disinfection. Because of this a high willingness of the user to perform the cleaning and disinfection correctly is demanded. After performing the cleaning using proteases, this protease solution usually is discarded and subsequently a separate disinfection phase is performed. This two-stage process is often considered to be cumbersome by users and promotes an improper mode of behavior due to a negligent use. Thus, for example, it may happen that the disinfecting step is forgotten and the lens is put on directly from the protease solution. In a different method a protease is added to the disinfecting solution, said protease, however, being added in such a high amount that the protease has to be eliminated by a physiological solution after the cleaning step. Otherwise, too much protease would remain within the contact lens matrix possibly resulting in irritations on the user's eye.

SUMMARY OF THE INVENTION

Consequently, it is the object of the present invention to provide systems which allow contact lenses to be cleaned and disinfected in a simple way.

Surprisingly, the object of the present invention is achieved in a simple way by a contact lens care agent having the features of the invention.

The contact lens care agent according to the invention has at least a first and a second compartment. The first compartment contains at least one agent, in particular metabolic protease, for removing or supporting the cleaning of protein-like deposits on a contact lens. The at least second compartment contains at least one agent being capable of neutralizing a contact lens disinfecting solution. Here, it is essential for the invention that the first compartment will dissolve quicker in a contact lens disinfecting solution than the second compartment. Both compartments can be subjected to the contact lens disinfecting solution at the same time. Proteases, in particular proteases of the serine type, are suited for the metabolic deposits removing agent. An enzyme class known as alkaline proteases, generally as subtilisin, is particularly preferred. Suitable enzymes have been characterized in EP 0 219 220.

The second compartment contains a contact lens disinfectant, wherein in the case of an aqueous hydrogen peroxide solution enzymes such as catalase or chemicals such as sodium dithionite are to be mentioned.

Preferably, the contact lens care agent according to the invention consists of a fist compartment and a second compartment. In one embodiment the first compartment encloses the second one completely. Preferably, however, the first compartment is enclosed by the second compartment not completely or only partially on all sides. Thereby, a simultaneous access of the disinfecting solution to the compartments is enabled. In a particular embodiment the first embodiment encloses the second compartment at least concentrically. In another embodiment of the contact lens care agent according to the invention said agent forms a formed piece having two axes being perpendicular to each other, wherein the first compartment is located around a first axis and the second compartment is located around a second axis. Preferably, the compartments are arranged rotationally symmetrical around one axis.

The disinfectant contacts the compartments and dissolves the first compartment quicker than the second compartment. The dissolution of the first compartment can be accelerated by additives. As additives in particular substances forming a readily soluble matrix or mixtures of substances generating effervescence in aqueous solution may be used. Especially preferred is the use of additives contributing to the formation of an isotonic solution subsequent to the dissolution of the compartments.

The second compartment may contain additives retarding a dissolution of the second compartment. This can be realized, e.g., by using substances or mixtures of substances which are more sparingly soluble than those being used in the first compartment.

DETAILED DESCRIPTION OF PREFERRED EMBODIMENTS

Figure 1:
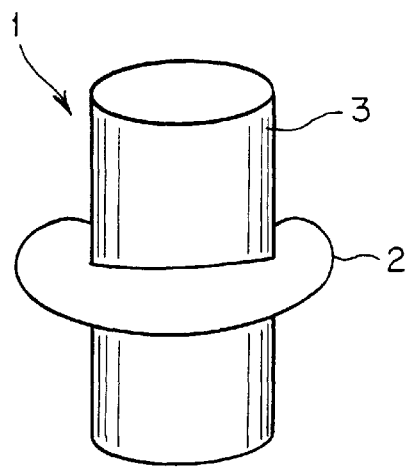
FIG. 1 shows a first embodiment of the invention in which a toroidal-shaped compartment surrounds a cylindrical-shaped compartment.

FIG. 1 illustrates a preferred embodiment of the contact lens care agent according to the invention. Here, a formed piece configured essentially cylindrically is the second compartment 3 containing subtilisin as protease. Said essentially cylindrical formed piece 3 containing subtilisin compressed within a usual tablet matrix is partially encompassed by the first compartment 2 having a toroidal shape, in the center of which the essentially cylindrical formed piece 3 of the first compartment is located.

Figure 2:
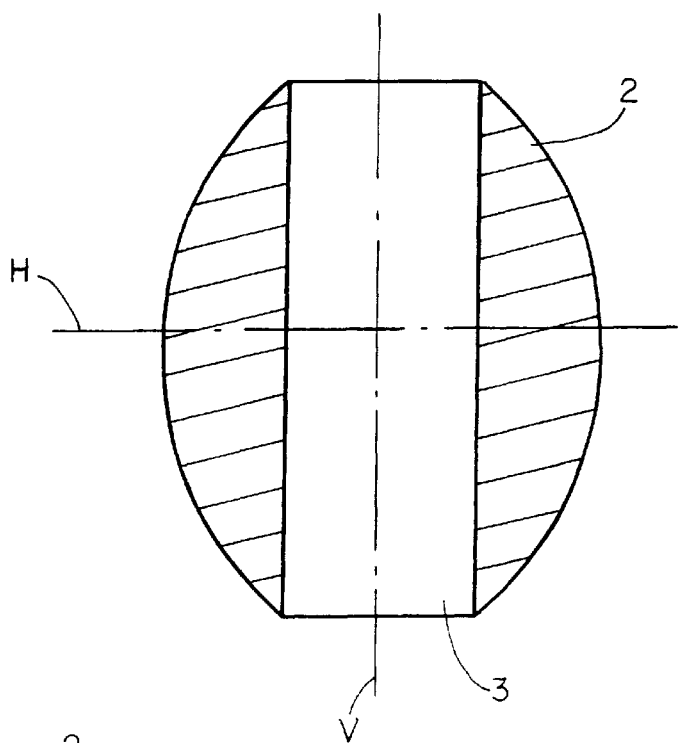
FIG. 2 shows a second embodiment, wherein the first compartment is bored through centrically and this bore is filled with the second compartment.

FIG. 2 illustrates another embodiment, wherein the first compartment 2 is bored through centrically and said bore is filled with the second compartment 3 so that the second compartment is partially encompassed.

The contact lens care agent is a formed piece having two axes V and H being perpendicular to each other, wherein the first compartment (2) is located around the first axis H and the second compartment (3) is located around the second axis V.

Figure 3:
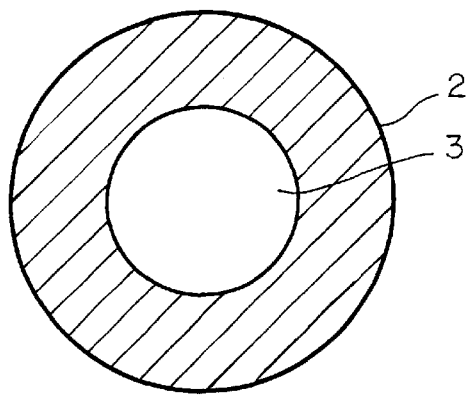
FIG. 3 shows another embodiment, wherein the first compartment encloses the second one completely.

FIG. 3 illustrates another embodiment, wherein the first compartment 2 encloses the second one 3 completely.

Initially, the user fills the aqueous disinfecting solution, preferably a 3% hydrogen peroxide solution, into a cleaning device known per se and adds the contact lens care agent according to the invention and the contact lenses to be cleaned and disinfected. The disinfecting solution will dissolve the compartment containing subtilisin so that the removal of any deposits existing on the lens begins. Simultaneously, the contact lens is disinfected by the action of the disinfectant $H_2O_2$. Depending on the embodiment also the second compartment, containing the agent neutralizing the disinfectant is dissolved more or less simultaneously. Due to the higher dissolution rate of the first compartment said first compartment will be dissolved completely when the second compartment has dissolved only partially within the disinfecting solution. Then, the catalase contained within the second compartment is further gradually dissolved into the disinfecting solution so that the catalase will increasingly cause the decomposition of the hydrogen peroxide within said compartment.

The contact lens care agent according to the invention provides a novel contact lens care system. Namely, on consultation with the contact lens fitter the user can define an individual cleaning procedure suited to the user's situation. Thus, e.g., if only moderate contaminations are present it is possible to perform the conventional disinfection on two successive days, whereas the contact lens care agent according to the invention is added at the third day in order to avoid performing the protein cleaning every day. Likewise, if heavier contaminations are present, removal of protein deposits can be effected on every other day using the contact lens care agent according to the invention. The contact lens care agent according to the invention is administered, e.g., in the form of blister packs, wherein in that case also tablets containing disinfectant neutralizers are offered. For example, there can be offered a blister pack offering, beginning with the contact lens care agent according to the invention in the form of tablets, e.g., two tablets which do not contain the agent, in particular the protease, for removing metabolic deposits, e.g., protein deposits. Only on the fourth day the blister pack will provide the contact lens care agent according to the invention, again followed by two tablets containing only the neutralizer.

The contact lens care agent according to the invention may contain the materials contained within the compartments also in the form of granulate, the compartments being designed, e.g., as capsules.

It may be preferred to perform the removal of the hydrogen peroxide not completely by defining the container volumes variably. With that, a residue of hydrogen peroxide will remain in the storage solution or cleaning solution. The advantage of the variability of the hydrogen peroxide volume to be employed is that during a longer storage period correspondingly more $H_2O_2$ containing solution can be provided so that decomposition will occur not completely and a residual content of $H_2O_2$ remains within the solution in order to provide a persistent bactericide and/or bacteriostatic environment within the solution. In particular, this residual content of hydrogen peroxide can be up to 0.8% by weight and, if required, less, e.g., up to 0.2% by weight. This offers the advantage that in particular during a longer storage of the lens within the storage solution there will be no subsequent microbic contamination as a continued bactericide and/or bacteriostatic environment will be present.

The agent can be adjusted such that there remains no or only a very low value of stimulus which remains controllable even with a very pronounced sensitivity of the eyes by a very short-time rinsing using appropriate commercial sodium chloride rinsing solutions.

What is claimed is:

1. A water-soluble, solid contact lens care agent (1) comprising at least a first (2) compartment and a second (3) compartment containing within the first compartment (2) at least one agent for removing or supporting the cleaning of metabolic deposits on a contact lens and within the second compartment (3) at least one agent being capable of neutralizing a contact lens disinfecting solution, wherein the first compartment (2) is dissolved faster within the contact lens disinfecting solution than the second compartment (3), and both compartments (2, 3) are simultaneously subjectable to the contact lens disinfecting solution due to the fact that the compartment (2) partially encompasses the second compartment (3).

2. The contact lens care agent according to claim 1, wherein two compartments (2, 3) are provided.

3. The contact lens care agent according to claim 1, wherein the dissolution of the first compartment (2) within the disinfecting solution is accelerated by additives.

4. The contact lens care agent according to claim 1, wherein the dissolution of the second compartment (3) within the disinfecting solution is retarded by additives.

5. The contact lens care agent according to claim 1, wherein the agent for neutralizing a contact lens disinfecting solution is present only in such an amount that a partial neutralization of the contact lens disinfectant takes place.

6. The contact lens care agent according to claim 1, wherein the first compartment (2) contains subtilisin and the second compartment (3) contains catalase.

7. The contact lens care agent according to claim 1, wherein the at least one agent for cleaning of metabolic deposits comprises a protease.

8. A water-soluble, solid contact lens care agent (1) comprising at least a first (2) compartment and a second (3) compartment containing within the first compartment (2) at least one agent for removing or supporting the cleaning of metabolic deposits on a contact lens and within the second compartment (3) at least one agent being capable of neutralizing a contact lens disinfecting solution, wherein the first compartment (2) is dissolved faster within the contact lens disinfecting solution than the second compartment (3), and both compartments (2, 3) are concentric simultaneously subjectable to the contact lens disinfecting solution due to the fact that the first compartment (2) partially encompasses the second compartment (3).

9. A water-soluble, solid contact lens care agent (1) comprising at least a first (2) compartment and a second (3) compartment containing within the first compartment (2) at least one agent for removing or supporting the cleaning of metabolic deposits on a-contact lens and within the second compartment (3) at least one agent being capable of neutralizing a contact lens disinfecting solution, wherein the first compartment (2) is dissolved faster within the contact lens disinfecting solution than the second compartment (3), and both compartments (2, 3) are simultaneously subjectable to the contact lens disinfecting solution due to the fact that the first compartment (2) partially encompasses the second compartment (3); and the contact lens care agent is a formed piece having two axes being perpendicular to each other, wherein the first compartment (2) is located around a first axis and the second compartment (3) is located around a second axis.

* * * * *